United States Patent [19]
Muraoka et al.

[11] Patent Number: 6,077,528
[45] Date of Patent: Jun. 20, 2000

[54] PERCUTANEOUS PREPARATION

[75] Inventors: Takateru Muraoka; Keigo Inosaka; Hitoshi Akemi; Hiroko Ishitani; Saburo Otsuka, all of Ibaraki; Yoshiteru Takahashi, Hirakata, all of Japan

[73] Assignees: Nitto Denko Corporation, Osaka; Kanebo, Ltd., Tokyo, both of Japan

[21] Appl. No.: 09/194,522

[22] PCT Filed: May 26, 1997

[86] PCT No.: PCT/JP97/01781

§ 371 Date: Nov. 24, 1998

§ 102(e) Date: Nov. 24, 1998

[87] PCT Pub. No.: WO97/45121

PCT Pub. Date: Dec. 4, 1997

[30] Foreign Application Priority Data

May 29, 1996 [JP] Japan .................................. 8-134914

[51] Int. Cl.[7] .............................. A61F 13/02; A61K 9/70; C07D 403/04

[52] U.S. Cl. ........................... 424/448; 424/449; 544/370
[58] Field of Search ..................................... 424/448, 449; 544/370

[56] References Cited

FOREIGN PATENT DOCUMENTS 55-131075  10/1980  Japan .
7-48258   2/1995   Japan .

*Primary Examiner*—Johann Richter
*Assistant Examiner*—Ebenezer Sackey
*Attorney, Agent, or Firm*—Leydig, Voit & Mayer, Ltd.

[57] ABSTRACT

The present invention relates to a percutaneous preparation comprising an adhesive layer formed on at least one side of a substrate, the layer containing an acrylic copolymer, 6-amino-5-chloro-1-isopropyl-2-(4-methyl-1-piperazinyl) benzimidazole or an acid addition salt thereof, and 2-mercaptobenzimidazole. This preparation exhibits superior percutaneous absorption of the benzimidazole compound and long sustention of efficacy, and shows an improved stability of the active ingredient, benzimidazole compound, in the preparation.

5 Claims, No Drawings

PERCUTANEOUS PREPARATION

This application is a 371 of PCT/JP97/01781 filed on May 26, 1997.

FIELD OF THE INVENTION

The present invention relates to a percutaneous preparation that can maintain 6-amino-5-chloro-1-isopropyl-2-(4-methyl-1-piperazinyl)benzimidazole or an acid addition salt thereof stably in the preparation and that enables continuous and percutaneous administration thereof to a living body.

BACKGROUND ART

Due to the superior serotonin$_3$ receptor antagonistic action, 6-amino-5-chloro-1-isopropyl-2-(4-methyl-1-piperazinyl)benzimidazole and an acid addition salt thereof (hereinafter they are also referred to as benzimidazole compound) of the formula (1):

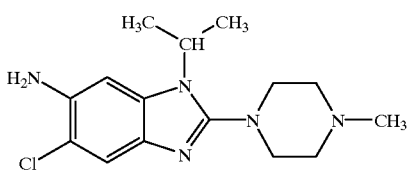

are known to be useful compounds as antiemetic agents against emesis caused by cancer chemotherapy using cisplatin and the like (Japanese Patent Unexamined Publication No. 17449/1993). Also, it has been already known that a percutaneous preparation containing a benzimidazole compound as an active ingredient exhibits serotonin$_3$ receptor antagonistic action upon percutaneous absorption of said benzimidazole compound (Japanese Patent Unexamined Publication No. 48258/1995).

However, a percutaneous preparation containing the above-mentioned benzimidazole compound as an active ingredient is unsatisfactory in the stability of the benzimidazole compound, which is the main drug, contained in the preparation.

DISCLOSURE OF THE INVENTION

It is therefore an object of the present invention to provide a percutaneous preparation superior in percutaneous absorption of benzimidazole compound and duration of efficacy, that exhibits an improved stability of the benzimidazole compound (which is as an active ingredient) in the preparation.

That is, the present invention provides the following.

(1) A percutaneous preparation comprising an adhesive layer formed on at least one side of a substrate, said layer comprising an acrylic copolymer, a benzimidazole compound and 2-mercaptobenzimidazole.

(2) The percutaneous preparation of (1), wherein the adhesive layer comprises the acrylic copolymer, a fatty acid ester miscible with said acrylic copolymer, a benzimidazole compound and 2-mercaptobenzimidazole.

(3) The percutaneous preparation of (2), wherein the adhesive layer has an acrylic copolymer: fatty acid ester weight ratio of 1:0.1–1:1.

(4) The percutaneous preparation of (2), wherein the adhesive layer has an acrylic copolymer: fatty acid ester weight ratio of 1:0.25–1:2, and said acrylic copolymer is crosslinked.

(5) The percutaneous preparation of (4), wherein the acrylic copolymer is crosslinked by at least one kind of a crosslinking agent selected from the group consisting of an alcholate and a metal chelate, both comprising titanium or aluminum, and a trifunctional isocyanate.

By forming a percutaneous preparation comprising an acrylic copolymer as a base material for a benzirmidazole compound, the benzimidazole compound is percutaneously absorbed to exhibit superior serotonin$_3$ receptor antagonistic action that lasts for an extended period of time. In particular, a percutaneous preparation further comprising a fatty acid ester alleviates or disperses the stress that works on the skin surface when removing said preparation. As a result, adhesion to the skin and stimulation to the skin can be balanced well. Moreover, addition of 2-mercaptobenzimidazole to said preparation improves the stability of the benzimidazole compound, which is an active ingredient, in the preparation.

While the substrate to be used for the inventive percutaneous preparation is free of any particular limitation, a preferable substrate does not permit decrease of the contents of the benzimidazole compound, 2-mercaptobenzimidazole and fatty acid ester in the adhesive layer, which is caused by the release thereof from the rear surface through the substrate. Thus, a substrate made from a material impermeable to these ingredients is preferable.

Specifically, used is a single film or a laminate film of polyesters such as polyethylene terephthalate, polyamides such as nylon, polyolefins such as polyethylene and polypropylene, poly(vinyl chloride), thermoplastic poly(vinyl chloride), thermoplastic vinyl acetate-vinyl chloride copolymer, poly(vinylidene chloride), ethylene-vinyl acetate copolymer, cellulose acetate, ethyl cellulose, ethylene-ethyl acrylate copolymer, polytetrafluoroethylene, polyurethane, ionomer resin, metal foils such as aluminum foil, and the like.

The thickness of the substrate is such that the percutaneous preparation maintains a soft texture, which is typically 1–25 μm, preferably 1–15 μm.

For an improved adhesion (anchor effect) of the adhesive layer to the substrate, particularly when the adhesive layer is a gel containing a fatty acid ester to be mentioned later, said substrate is preferably formed into a laminate film comprising a porous film and a film substantially free of pores, which is made from the above-mentioned materials, and the adhesive layer is formed on the porous film side.

Such porous film is free of any particular limitation as long as it shows an improved anchor effect of the adhesive layer, and exemplified by paper, woven fabric, nonwoven fabric, mechanically perforated film and the like, with particular preference given to paper, woven fabric and nonwoven fabric.

A preferable thickness of the porous film in consideration of an improved anchor effect and the flexibility of the percutaneous preparation as a whole is 10–500 μm, and a thin preparation, such as a plaster and an adhesive tape, preferably has a thickness of 10–200 μm.

When a woven fabric or a nonwoven fabric is used as the porous film, the basic weight is 5–30 g/m$^2$, preferably 8–20 g/m$^2$, for an improved anchor effect. It is also possible to use a comparatively permeable substrate to control the drug releasability of the percutaneous preparation.

The percutaneous preparation of the present invention comprises the adhesive layer to be mentioned later, which is formed on at least one side of the above-mentioned substrate.

Said adhesive layer contains an acrylic copolymer, a benzimidazole compound and 2-mercaptobenzimidazole.

The benzimidazole compound to be contained in the percutaneous preparation of the present invention includes a compound of the above-mentioned formula (1) and an acid addition salt thereof. Said benzimidazole compound can be produced by a method known per se, for example, by the method described in the above-mentioned Japanese Patent Unexamined Publication No. 17449/1993.

The acid addition salt of the benzimidazole compound is preferably exemplified by hydrochloride, sulfate, maleate, fumaratea and the like. When a pharmacologically acceptable acid addition salt of the benzimidazole compound is used, an organic base (e.g., ethanolamine and the like) or an inorganic base (e.g., sodium hydroxide and sodium carbonate and the like) may be concurrently added to the adhesive layer, whereby said acid addition salt becomes a free base in the adhesive layer.

While the content of the benzimidazole compound can be appropriately determined according to the administration object and the like, it is generally about 0.1–30 wt %, preferably 0.5–10 wt %, of the adhesive layer. When the content is less than 0.1 wt %, the release of a drug in an amount effective for the treatment may not be expected, whereas when it exceeds 30 wt %, economical disadvantages may be caused.

The 2-mercaptobenzimidazole to be used in the present invention acts on certain components (e.g., residual monomer, residual polymerization initiator, additive, impurity and the like) contained in the adhesive in trace amounts. They cause interactions (e.g., oxidative decomposition, optical resolution, coloring and the like) with the above-mentioned benzimidazole compound. The 2-mercaptobenzimidazole inhibits reactions between the benzimidazole compound and the components contained in the adhesive in trace amounts, thereby affording an improved stability of the benzimidazole compound in the preparation.

While the content of 2-mercaptobenzimidazole can be appropriately determined according to the kind of adhesive, the intensity of the interaction and the like, it is generally about 0.01–5.0 wt %, preferably 0.02–3.0 wt %, and more preferably 0.03–2.0 wt %, of the adhesive.

When the content of 2-mercaptobenzimidazole is too small, sufficient inhibitory activity is difficult to achieve. On the other hand, when 2-mercaptobenzimidazole content is too great, other components in the adhesive (e.g., crosslinking agent and the like) and the benzimidazole compound may interact. In addition, other reaction products may occur that decrease stability of the preparation.

The acrylic copolymer to be used in the present invention is a copolymer produced by copolymerization of alkyl acrylate and/or alkyl methacrylate, wherein the alkyl group has 4 or more carbon atoms, [hereinafter alkyl acrylate and/or alkyl methacrylate are/is also referred to as alkyl (meth)acrylate], as a main component.

With regard to alkyl (meth)acrylate, alkyl is specifically exemplified by linear or branched alkyl having 4 to 13 carbon atoms, such as butyl, pentyl, hexyl, heptyl, octyl, nonyl, decyl, undecyl, dodecyl, tridecyl and the like, which may be used alone or in combination. Besides the above-mentioned alkyl (meth)acrylate, alkyl having 1 to 3 carbon atoms and alkyl (meth)acrylate, wherein the alkyl group has 14 or more carbon atoms, may be concurrently used.

The monomer to be copolymerized with the above-mentioned alkyl (meth)acrylate is exemplified by carboxyl group-containing monomer [e.g., (meth)acrylate, itaconic acid, maleic acid and the like]; sulfoxyl group-containing monomer [e.g., styrenesulfonic acid, allylsulfonic acid, sulfopropyl (meth)acrylate, (meth)acryloyloxynaphthalenesulfonic acid, acrylamide methylpropanesulfonic acid and the like]; hydroxyl group-containing monomer [e.g., hydroxyethyl (meth)acrylate, hydroxypropyl (meth)acrylate and the like]; amide group-containing monomer [e.g., (meth)acrylamide, dimethyl (meth)acrylamide, N-butylacrylamide, N-methylol (meth)acrylamide, N-methylolpropane (meth)acrylamide and the like]; aminoalkyl group-containing monomer [e.g., aminoethyl (meth)acrylate, dimethylaminoethyl (meth)acrylate, tert-butylaminoethyl (meth)acrylate and the like]; monomer having a functional group at the side chain such as alkoxyalkyl (meth)acrylate [e.g., methoxyethyl (meth)acrylate, ethoxyethyl (meth)acrylate and the like]; alkoxyl group (or ether bond at the side chain)-containing (meth)acrylate [e.g., tetrahydroflufuryl (meth)acrylate, methoxyethylene glycol (meth)acrylate, methoxydiethylene glycol (meth)acrylate, methoxypolyethylene glycol (meth)acrylate, methoxypolypropylene glycol (meth)acrylate and the like]; and the like. Besides the above-mentioned, other copolymerizable monomers such as vinyl monomers [e.g., (meth)acrylonitrile, vinyl acetate, vinyl propionate, N-vinyl 2-pyrrolidone, methyl o-pyrrolidone, methyl vinyl pyrrolidone, vinylpyridine, vinylpiperidone, vinyl pyrimidine, vinyl piperazine, vinyl pyrazine, vinyl pyrrole, vinyl imidazole, vinyl caprolactum, vinyl oxazole and vinyl morpholine] can be used. These may be copolymerized alone or in combination. In consideration of adhesion to the skin and cohesion as adhesive properties, releasability of the benzimidazole compound, and reactivity during the crosslinking treatment of the adhesive layer, at least one kind of the carboxyl group-containing monomers and hydroxyl group-containing monomers is preferably used as an essential component from among the above-mentioned monomers, and copolymerized as necessary with other copolymerizable monomers exemplified above.

These copolymerizable monomers can be appropriately selected and used for the adjustment of cohesion of an adhesive layer, adjustment of solubility and releasability of benzimidazole compound.

The amount of the monomer to be copolymerized other than alkyl (meth)acrylate is optionally determined according to the object. In general, it is 2–50 wt %, preferably 3–40 wt %, of the entire monomer to prepare an acrylic copolymer.

The acrylic copolymer to be used in the present invention can be synthesized by a method known per se using the above-mentioned alkyl (meth)acrylate and monomers copolymerizable therewith. For example, the copolymer is obtained by solution polymerization, emulsion polymerization, bulk polymerization, suspension polymerization and the like.

When a rubber or silicone polymer such as natural rubber and synthetic rubber is used instead of an acrylic copolymer, the solubility, releasability and/or permeation through the skin of the drug may become strikingly poor, and the use thereof is not desirable. Said polymer tends to show insufficient miscibility with a fatty acid ester in the gel type adhesive layer to be mentioned later, or cause difficulty in controlling the amount of the functional group involved in crosslinking reaction, thus maldng a reproductive crosslinking treatment unattainable.

The adhesive layer to be used in the present invention is preferably a gel type adhesive layer containing a fatty acid ester miscible with the above-mentioned acrylic copolymer. In this way, excellent adhesion to the skin surface, low irritation to the skin and fine shape retention property can be attained.

In said gel type adhesive layer, said acrylic copolymer has been preferably crosslinked.

The fatty acid ester to be used in the present invention is miscible with the above-mentioned acrylic copolymer. It plasticizes the adhesive layer and affords a feel of softness, whereby, when the adhesive layer is peeled off from the skin surface, a pain and/or irritation to the skin due to the adhesion to the skin can be reduced.

Hence, the fatty acid ester only needs to have a plasticizing effect. For an improved percutaneous absorption of the co-existing benzimidazole compound, it preferably has an absorption promoting action as well.

Specific examples of such fatty acid ester include adipates such as diisopropyl adipate, diisobutyl adipate, dioctyl adipate and the like; sebacates such as diethyl sebacate, diisopropyl sebacate and the like; glycerol fatty acid ester; myristates such as isopropyl myristate, isotridecyl myristate, tetradecyl myristate and the like; laurates such as ethyl laurate, hexyl laurate and the like; oleates such as ethyl oleate, oleyl oleate, decyl oleate and the like; palmitates such as isopropyl palmitate, octyl palmitate, hexadecyl palmitate, isostearyl palmitate and the like; triethyl citrate; acetates such as benzyl acetate, n-butyl acetate and the like; stearic polyoxylsorbitan fatty acid ester; propylene glycol esters of fatty acid; and the like. They may be added alone or in combination. Of these, a fatty acid ester comprising a higher fatty acid having 8–18, preferably 10–16, carbon atoms and a lower alcohol having 1–4 carbon atoms is preferably used, in consideration of the miscibility with the above-mentioned acrylic copolymer and nonvolatile property and non-decomposability in a heat treatment during production of a pharmaceutical preparation.

When an ester of a fatty acid, such as myristic acid, adipic acid, sebacic acid, palmitic acid and the like, which cannot dissolve benzimidazole compounds easily, is used, a solubilizer such as N,N-dimethylacetamide, diethanolamine, triacetin, isopropanol, 1,2-dichloromethane, isobutanol and the like is preferably used.

With respect to a gel type adhesive layer containing a fatty acid ester, the weight ratio of (acrylic copolymer:fatty acid ester) without crosslinking is 1:0.1–1:1, preferably 1:0.1–1:0.8. When crosslinking is done, it is 1:0.25–1:2, which is preferably 1:0.4–1:1.8, more preferably 1:0.6–1:1.8, for less irritation to the skin, wherein a greater amount of fatty acid ester is preferred.

The method for crosslinking the acrylic copolymer is exemplified by chemical crosslinking treatment generally using a crosslinking agent such as polyisocyanate compound, organic peroxide, organic metal salt, alcoholate, metal chelate, multifunctional compound and the like.

Of these crosslinking means, the use of an organic peroxide may lead to the decomposition of the benzimidazole compound, and the use of highly reactive isocyanates, metal salt and/or organic metal salt used for normal crosslinking reaction may cause thickening of the solution after addition and degrade the workability. It may be possible to previously polymerize a multifunctional monomer, such as diacrylate, with an acrylic copolymer, but again not without a possibility of increasing viscosity of the solution.

In the present invention, therefore, an alcoholate or metal chelate comprising titanium or aluminum, or a trifunctional isocyanate is preferably used from among these crosslinking agents, in view of reactivity and handling property. These crosslinking agents are free of thickening of the solution before coating and drying, and exhibit extremely superior workability.

In this case, the crosslinking agent is generally contained in an amount of about 0.01–2 parts by weight, preferably 0.05–1.5 parts by weight, per 100 parts by weight of the acrylic copolymer.

Even when the acrylic copolymer does not have a functional group reactive with the above-mentioned crosslinking agent, monomer can be hydrolyzed by an alkali treatment of the substance to be crosslinked, whereby said copolymer can be modified to have a structure permitting crosslinking.

The adhesive layer to be used in the present invention preferably contains a benzimidazole compound and 2-mercaptobenzimidazole in the above-mentioned acrylic copolymer. Instead of containing them in the acrylic copolymer from the start, the benzimidazole compound and 2-mercaptobenzimidazole may be directly, or after dissolution in a suitable solvent, disposed at the interface between the acrylic copolymer layer and the substrate, and the periphery of the preparation is sealed, whereby the benzimidazole compound and 2-mercaptobenzimidazole are released gradually into the acrylic copolymer layer to form the adhesive layer in the present invention. In this way, by gradually forming an adhesive layer with an acrylic copolymer layer and a drug-containing layer, the decomposition of a drug during days of storage can be more effectively suppressed. For sealing of the periphery of the preparation, an acrylic copolymer layer may be used, or a microporous film may be interposed between the drug-containing layer and the acrylic copolymer layer and said microporous film and a substrate are heat adhered for sealing, or other methods may be used. By interposing a microporous film between the drug-containing layer and the acrylic copolymer layer, a stringent control of the drug release can be achieved.

The adhesive layer to be used in the present invention preferably has an adhesion strength as expressed by the adhesion to a Bakelite board of approximately 300–2000 g/24 mm width. The adhesion strength of a gel type adhesive layer containing a fatty acid ester as expressed by the adhesion to a Bakelite board is approximately 40–300 g/24 mm width.

In the present invention, the adhesion strength of the adhesive layer is measured according to JIS Z 0237. To be specific, the percutaneous preparation of the present invention is cut into 24 mm wide strip samples which are adhered to a Bakelite board and press-adhered by a single reciprocation of a roller (load 850 g) thereon. After adhesion, the board is left standing for 20 min at 23° C.×60% RH. Under the same atmosphere, a tensilon tester is used to peel off the sample in the direction forming an angle of 180° at a rate of 300 mm/min and the peel strength at that time is measured.

The thickness of said adhesive layer is generally 10–200 μm, preferably 15–150 μm.

The said adhesive layer may contain known additives such as thickener, absorption promoter, surfactant, plasticizer, filler, deterioration preventive and the like.

The method of producing the percutaneous preparation of the present invention is not particularly limited. For example, an acrylic copolymer, (a fatty acid ester), 2-mercaptobenzimidazole, a benzimidazole compound and (a crosslinking agent) are dissolved or dispersed in this order in a solvent, the obtained solution or dispersion is applied to at least one surface of a substrate and dried to form an adhesive layer on the surface of the substrate. Alternatively, the obtained solution or dispersion is applied to a release sheet for protection and dried to form an adhesive layer on the release sheet. Thereafter, a substrate is adhered to the adhesive layer.

In the percutaneous preparation of the present invention, a release sheet can be laminated on the surface of an adhesive layer to prevent unnecessary contact of the adhesive layer with instruments or containers during production, transport or storage, as well as to prevent degradation of the preparation. The release sheet is peeled off to expose the surface of the adhesive layer, which is then adhered to the skin for administration.

The release sheet is not particularly limited as long as it can be released easily from the adhesive layer during use. For example, a film of polyester, poly(vinyl chloride), poly(vinylidene chloride), polyethylene terephthalate and the like, wherein a silicone treatment is applied to the contact surface with the adhesive layer, a laminate film made of polyolefin and woodfree paper or glassine paper, and the like are used.

The thickness of the release sheet is generally not more than 1000 μm, preferably 30–200 μm.

While the dose of the percutaneous preparation of the present invention varies depending on the age, body weight, symptom and the like of patients, a typical administration involves adhesion of the preparation containing 1–1000 mg/administration of the benzimidazole compound to the skin (1–50 cm$^2$) of an adult about twice a day to once in 7 days.

The present invention is explained in more detail by way of examples, which are not to be construed as limiting the invention.

In the following description, "part" and "%" mean "parts by weight" and "wt %", respectively.

[Preparation of acrylic copolymer A]

2-Ethylhexyl acrylate (95 parts) and acrylic acid (5 parts) were copolymerized in ethyl acetate under an inert gas atmosphere to prepare an acrylic copolymer A solution.

[Preparation of acrylic copolymer B]

2-Ethylhexyl acrylate (72 parts), N-vinyl 2-pyrrolidone (25 parts) and acrylic acid (3 parts) were copolymerized in ethyl acetate under an inert gas atmosphere to prepare an acrylic copolymer B solution.

[Acrylic copolymer C]

Primal N-580 (NF-1) (ROHM AND HAAS JAPAN KK.), which is an emulsion of a copolymer of methacrylic acid and n-butyl acrylate in an aqueous amino acetate solution, was used as an acrylic copolymer C solution.

[Preparation of rubber adhesive]

High molecular weight polyisobutylene (28.5 parts, Exxon Chemical, VISTANEX MML-80, viscosity average molecular weight 990,000), low molecular weight polyisobutylene (43 parts, NIPPON PETROCHEMICALS CO., LTD., HIMOL 6H, viscosity average molecular weight 60,000), polybutene (8.5 parts, NIPPON PETROCHEMICALS CO., LTD., HV-300, viscosity average molecular weight 1,260) and alicyclic petroleum resin (20 parts, ARAKAWA CHEMICAL INDUSTRIES LTD., Arkon P-100, softening point 100° C.) were dissolved in hexane to prepare a polyisobutylene adhesive solution.

[Silicon adhesive]

SILASCON 360 (Dow Corning Corporation), which is a linear polymer of poly(dimethylsiloxane), was used as a silicon adhesive solution.

The acrylic copolymer solutions A, B obtained above were applied to a release paper in such a manner that the thickness after drying was 100 μm, so that the amount of residual monomer could be reduced, and dried at 100° C. for 10 minutes. The acrylic copolymer was recovered, re-dissolved in ethyl acetate and used.

EXAMPLES 1–5, COMPARATIVE EXAMPLES 1–7

According to the composition proportions shown in Table 1, respective viscous solutions were prepared. The obtained solutions were applied to a polyester release sheet (75 μm thick) to the thickness after drying of 60 μm, and dried to give an adhesive layer.

This adhesive layer was adhered to a laminate film consisting of polyester nonwoven fabric (basic weight 12 g/m$^2$) and polyester film (2 μm thick) on the nonwoven fabric side to give a percutaneous preparation.

The amount of the crosslinking agent in Examples 3 and 4 and Comparative Examples 5 and 6 was 0.6 part per 100 parts of the solid component of the acrylic copolymer. After adhesion to a substrate (laminate film) as mentioned above, the film was heated at 70° C. for 48 hours for crosslinking.

TABLE 1

|  | Polymer (%) |  | Benzimidazole compound (%) | 2-Mercaptobenz-imidazole (%) | IPM (%) | Crosslinking agent |
|---|---|---|---|---|---|---|
| Ex. 1 | Acrylic copolymer A | 89.5 | 10 | 0.5 | — | — |
| Ex. 2 | Acrylic copolymer B | 89.5 | 10 | 0.5 | — | — |
| Ex. 3 | Acrylic copolymer A | 44.5 | 5 | 0.5 | 50 | Al chelate |
| Ex. 4 | Acrylic copolymer B | 44.5 | 5 | 0.5 | 50 | Al chelate |
| Ex. 5 | Acrylic copolymer C | 64.5 | 5 | 0.5 | 30 | — |
| Comp. Ex. 1 | Rubber copolymer | 90 | 10 | — | — | — |
| Comp. Ex. 2 | Silicon copolymer | 90 | 10 | — | — | — |
| Comp. Ex. 3 | Acrylic copolymer A | 90 | 10 | — | — | — |
| Comp. Ex. 4 | Acrylic copolymer B | 90 | 10 | — | — | — |
| Comp. Ex. 5 | Acrylic copolymer A | 45 | 5 | — | 50 | Al chelate |
| Comp. Ex. 6 | Acrylic copolymer B | 45 | 5 | — | 50 | Al chelate |
| Comp. Ex. 7 | Acrylic copolymer C | 65 | 5 | — | 30 | — |

IPM: isopropyl myristate
Al chelate: aluminum ethyl acetoacetate diisopropylate
benzimidazole compound: 6-amino-5-chloro-1-isopropyl-2-(4-methyl-1-piperazinyl)benzimidazole The percutaneous preparations prepared in the above Examples and Comparative Examples 1, 2 weere subjected to the following skin permeation test.

[Skin permeation test]

Each preparation was adhered to the shed skin of a python (hydrated overnight in distilled water) and set on a cell for skin permeation test (effective area 0.2826 cm$^2$). The permeation test was performed for 24 hours. Deaerated distilled water was used as a receptor solution and flown at a flow rate of 2 ml/hr. At predetermined times (4, 8, 12, 16, 20 and 24 hr), sample receptor solutions were taken. The concentration of the permeated benzimidazole compound was quantitatively determined by high performance liquid chromatography and the amount of the permeated benzimidazole compound was calculated. High performance liquid chromatography was performed under the following conditions.

column: Merck Lichrospher 100 RP-18
    endcapped (5 μm) [125 mm×4.0 mm, manufactured by Merck]
mobile phase: mixture (pH=3.5) of water 550 vol, acetonitrile 450 vol and sodium dodecylsulfate 2.0 g
column temperature: 23° C.±2° C.
flow rate: 2.0 ml/min
detection method: measurement of absorbance at UV 315 nm The accumulated amounts (average of 3 per group, unit μg/cm$^2$) of the benzimidazole compound that passed through the skin at 4, 8, 12, 16, 20 and 24 hours after administration are shown in Table 2. Comparative Examples 3–7 showed nearly the same accumulated skin permeation amounts as in Examples 1–5.

TABLE 2

| | Accumulated skin permeation amount (μg/cm$^2$) at certain hours after administration | | | | | |
|---|---|---|---|---|---|---|
| | 4 h | 8 h | 12 h | 16 h | 20 h | 24 h |
| Ex. 1 | 0.00 | 0.02 | 1.25 | 3.25 | 5.35 | 7.50 |
| Ex. 2 | 0.00 | 0.05 | 1.65 | 4.05 | 6.25 | 8.65 |
| Ex. 3 | 0.47 | 3.22 | 7.56 | 11.96 | 15.85 | 26.43 |
| Ex. 4 | 0.24 | 4.69 | 11.85 | 18.55 | 24.63 | 30.18 |
| Ex. 5 | 0.00 | 1.08 | 3.67 | 6.68 | 9.92 | 13.08 |
| Com.Ex. 1 | 0.00 | 0.00 | 0.00 | 0.00 | 0.05 | 0.15 |
| Com.Ex. 2 | 0.00 | 0.00 | 0.00 | 0.05 | 0.13 | 0.25 |

The percutaneous preparations prepared in the above Examples and Comparative Examples were subjected to the following stability test.

[Stability Test]

The presence or absence of a decomposed product of the benzimidazole compound in each percutaneous preparation was confirmed immediately after the production of the preparation and after 1 month airtight storage at 50° C.

Each preparation was punched out into 10 cm$^2$ and narrowly cut, which was followed by immersion in methanol and extraction by shaking. The extract solution was quantitatively determined by high performance liquid chromatography under the above-mentioned conditions, whereby the presence or absence of decomposed product was confirmed. The results are shown in Table 3.

TABLE 3

| | Presence of decomposed product | |
|---|---|---|
| | Immediately after preparation | After 1 month airtight storage at 50° C. |
| Ex. 1 | none | none |
| Ex. 2 | none | none |
| Ex. 3 | none | none |
| Ex. 4 | none | none |
| Ex. 5 | none | none |
| Com. Ex. 1 | none | none |
| Com. Ex. 2 | none | none |
| Com. Ex. 3 | found | found |
| Com. Ex. 4 | found | found |
| Com. Ex. 5 | found | found |
| Com. Ex. 6 | found | found |
| Com. Ex. 7 | none | found |

According to the present invention, there are provided a percutaneous preparation wherein a benzimidazole compound is percutaneously absorbed to show superior serotonin$_3$ receptor antagonistic action and said action is long-lasting, and a percutaneous preparation that has improved the stability of the active ingredient, benzimidazole compound, in the preparation.

This application is based on application No. 134914/1996 filed in Japan, the content of which is incorporated hereinto by reference.

What is claimed is:

1. A percutaneous preparation comprising an adhesive layer formed on at least one side of a substrate, said layer comprising an acrylic copolymer, 6-amino-5-chloro-1-isopropyl-2-(4-methyl-1-piperazinyl)benzimidazole or an acid addition salt thereof, and 2-mercaptobenzimidazole.

2. The percutaneous preparation of claim 1, wherein the adhesive layer comprises the acrylic copolymer, a fatty acid ester miscible with said acrylic copolymer, 6-amino-5-chloro-1-isopropyl-2-(4-methyl-1-piperazinyl)-benzimidazole or an acid addition salt thereof, and 2-mercaptobenzimidazole.

3. The percutaneous preparation of claim 2, wherein the adhesive layer has an acrylic copolymer: fatty acid ester weight ratio of 1:0.1–1:1.

4. The percutaneous preparation of claim 2, wherein the adhesive layer has an acrylic copolymer: fatty acid ester weight ratio of 1:0.25–1:2, and said acrylic copolymer is crosslinked.

5. The percutaneous preparation of claim 4, wherein the acrylic copolymer is crosslinked by at least one crosslinking agent selected from the group consisting of an alcholate and a metal chelate, both comprising titanium or aluminum, and a trifunctional isocyanate.

\* \* \* \* \*